(12) United States Patent
Ge

(10) Patent No.: US 9,724,543 B2
(45) Date of Patent: Aug. 8, 2017

(54) ANTIPERSPIRANT PRODUCTS COMPRISING ACTIVE ANTIPERSPIRANT COMPOUNDS SURFACE TREATED WITH HYDROPHOBIZING AGENTS AND METHODS FOR MANUFACTURING THE SAME

(75) Inventor: Haiyan Ge, Scottsdale, AZ (US)

(73) Assignee: Henkel IP & Holding GmbH (DE)

( * ) Notice: Subject to any disclaimer, the term of this patent is extended or adjusted under 35 U.S.C. 154(b) by 1506 days.

(21) Appl. No.: 12/857,232

(22) Filed: Aug. 16, 2010

(65) Prior Publication Data

US 2012/0039968 A1 Feb. 16, 2012

(51) Int. Cl.
| | | |
|---|---|---|
| A61K 8/02 | (2006.01) | |
| A61K 8/92 | (2006.01) | |
| A61K 8/58 | (2006.01) | |
| A61K 8/25 | (2006.01) | |
| A61Q 15/00 | (2006.01) | |
| B29C 39/38 | (2006.01) | |
| A61K 8/28 | (2006.01) | |
| A61K 8/29 | (2006.01) | |
| A61K 8/36 | (2006.01) | |
| A61K 8/89 | (2006.01) | |

(52) U.S. Cl.
CPC ............ *A61Q 15/00* (2013.01); *A61K 8/0241* (2013.01); *A61K 8/28* (2013.01); *A61K 8/29* (2013.01); *A61K 8/361* (2013.01); *A61K 8/89* (2013.01); *A61K 2800/58* (2013.01); *A61K 2800/612* (2013.01); *A61K 2800/614* (2013.01)

(58) Field of Classification Search
USPC .............................................. 424/47, 59, 66
See application file for complete search history.

(56) References Cited

U.S. PATENT DOCUMENTS

| | | | |
|---|---|---|---|
| 4,877,604 A | | 10/1989 | Schlossman |
| 5,232,689 A | * | 8/1993 | Katsoulis et al. .............. 424/66 |
| 2005/0196360 A1 | * | 9/2005 | Comte et al. .................. 424/59 |

FOREIGN PATENT DOCUMENTS

WO    WO2005/099651 A1    10/2005

OTHER PUBLICATIONS

Kobo Products, Inc.,Triethoxy Caprylylsilane Treatment, Technical Literature Ref 11S-005, Oct. 20, 2008, Kobo Products, Inc.,USA.
Kobo Products, Inc., Titanate Treatment, Technical Literature Ref ITT-001, Feb. 10, 2009, Kobo Products, Inc., USA.

\* cited by examiner

*Primary Examiner* — Walter Webb
(74) *Attorney, Agent, or Firm* — P. Scott Smith

(57) ABSTRACT

Antiperspirant products comprising active antiperspirant compounds surface treated with hydrophobizing agents and methods for manufacturing such products are provided. In accordance with an exemplary embodiment, an antiperspirant product comprises a hydrophobic carrier and an active antiperspirant compound with a coating of a hydrophobizing agent.

14 Claims, No Drawings

ANTIPERSPIRANT PRODUCTS COMPRISING ACTIVE ANTIPERSPIRANT COMPOUNDS SURFACE TREATED WITH HYDROPHOBIZING AGENTS AND METHODS FOR MANUFACTURING THE SAME

FIELD OF THE INVENTION

The present invention generally relates to antiperspirant products and methods for manufacturing antiperspirant products, and more particularly relates to antiperspirant products comprising active antiperspirant compounds surface treated with hydrophobizing agents and methods for manufacturing the same.

BACKGROUND OF THE INVENTION

Antiperspirants are popular personal care products used to prevent or eliminate perspiration and body odor caused by perspiration. Antiperspirant sticks are desired by a large majority of the population because of the presence of active antiperspirant compounds that minimize or prevent the secretion of perspiration by blocking or plugging ducts of sweat-secreting glands, such as those located at the underarms. Antiperspirants typically comprise an active antiperspirant compound in a carrier that permits the antiperspirant product to be applied to the skin by swiping or rubbing the stick across the skin, typically of the underarm. Upon application, the carrier evaporates, releasing the active antiperspirant compound from the antiperspirant product to form plugs in the sweat ducts.

However, present day antiperspirant products present several drawbacks. For example, antiperspirant users often find antiperspirant products abrasive and/or irritating to the skin and are disappointed in the stickiness and slipperiness of the solid wax stick across the skin. In addition, the amount of the active antiperspirant compound in antiperspirant products is limited. The active antiperspirant compounds in antiperspirant products can be costly. In addition, the United States Food and Drug Administration has limited the amount of active antiperspirant compound that can be added to an antiperspirant product before the product is considered "clinical" and available only by prescription. Thus, methods are needed to enhance the effectiveness of active antiperspirant compounds without adding additional active antiperspirant compounds.

Accordingly, it is desirable to provide antiperspirant products that have enhanced antiperspirant efficacy. It is also desirable to provide antiperspirant products that have improved skin feel. In addition, it is desirable to provide methods for manufacturing such antiperspirant products. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

Antiperspirant products comprising active antiperspirant compounds surface treated with hydrophobizing agents and methods for manufacturing such products are provided. In accordance with an exemplary embodiment, an antiperspirant product comprises an active antiperspirant compound with a coating of a hydrophobizing agent and a hydrophobic carrier.

In accordance with another exemplary embodiment, a method for manufacturing an antiperspirant product comprises combining an active antiperspirant compound coated with a hydrophobizing agent and a carrier at a first temperature to form a mixture. At a second temperature less than the first temperature, the mixture is poured into molds and the mixture is cooled to a third temperature less than the second temperature.

In accordance with a further exemplary embodiment, an antiperspirant product comprises an active antiperspirant compound with a coating of a hydrophobizing agent, a hydrophobic carrier, stearyl alcohol, hydrogenated castor oil, and a suspending agent.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The various embodiments contemplated herein relate to an antiperspirant product with enhanced antiperspirant efficacy. In addition, or alternatively, various embodiments exhibit improved "skin feel." That is, when applied to the skin of a user, the antiperspirant product exhibits reduced slipperiness, i.e., reduced slip between the underarms, and improved glide. The term "glide" typically is used to denote the perceived friction between the antiperspirant product and the skin. The smoother the glide, or the less friction between the product and the skin, the more desirable the product is to users. It unexpectedly has been found that antiperspirant products that exhibit enhanced antiperspirant efficacy and/or improved skin feel can be achieved when manufactured with an active antiperspirant compound that has been surface treated with a hydrophobizing agent.

In this regard, the various embodiments of the antiperspirant products comprise a water-soluble active antiperspirant compound. Active antiperspirant compounds contain at least one active ingredient, typically metal salts, that are thought to reduce perspiration by diffusing through the sweat ducts of apocrine glands (sweat glands responsible for body odor) and hydrolyzing in the sweat ducts, where they combine with proteins to form an amorphous metal hydroxide agglomerate, plugging the sweat ducts so perspiration cannot diffuse to the skin surface. Some active antiperspirant compounds that may be used in the antiperspirant product include astringent metallic salts, especially inorganic and organic salts of aluminum, zirconium, and zinc, as well as mixtures thereof. Particularly preferred are aluminum-containing and/or zirconium-containing salts or materials, such as aluminum halides, aluminum chlorohydrates, aluminum hydroxyhalides, zirconyl oxyhalides, zirconyl hydroxyhalides, and mixtures thereof. Exemplary aluminum salts include those having the general formula $Al_2(OH)_aCl_b \cdot (H_2O)$, wherein a is from 2 to about 5; a and b total to about 6; x is from 1 to about 6; and wherein a, b, and x may have non-integer values. Exemplary zirconium salts include those having the general formula $ZrO(OH)_{2-a}Cl_a \cdot (H_2O)$, wherein a is from about 1.5 to about 1.87, x is from about 1 to about 7, and wherein a and x may both have non-integer values. Particularly preferred zirconium salts are those complexes that additionally contain aluminum and glycine, commonly known as ZAG complexes. These ZAG complexes contain aluminum chlorohydroxide and zirconyl hydroxy chloride conforming to the above-described formulas. Examples of active antiperspirant compounds suitable for use in the various embodiments contemplated herein include aluminum dichlorohydrate, aluminum-zirconium octachlorohydrate, aluminum sesquichlorohydrate, aluminum chlorohydrex propylene glycol complex, aluminum dichlorohydrex propylene glycol complex, aluminum sesquichlorohydrex propylene glycol complex, aluminum chlorohydrex polyethylene glycol complex, aluminum dichlorohydrex polyethylene glycol complex, aluminum sesquichlorohydrex polyethylene glycol complex, aluminum-zirconium trichlorohydrate, aluminum zirconium tetrachlorohydrate, aluminum zirconium pentachlorohydrate, aluminum zirconium octachlorohydrate, aluminum zirconium trichlorohydrex glycine complex, aluminum zirconium tetrachlorohydrex glycine complex, aluminum zirconium pentachlorohydrex glycine complex, aluminum zirconium octachlorohydrex glycine complex, zirconium chlorohydrate, aluminum chloride, aluminum sulfate buffered, and the like, and mixtures thereof. In a preferred embodiment, the active antiperspirant compound is aluminum zirconium trichlorohydrex glycine complex, aluminum zirconium pentachlorohydrex glycine complex, aluminum zirconium tetrachlorohydrate glycine complex, or aluminum zirconium octachlorohydrex glycine complex. In a more preferred embodiment, the antiperspirant product comprises an active antiperspirant compound at an active level of about 8 to about 30 wt. % (USP) of the total antiperspirant product. As used herein, weight percent (USP) or wt. % (USP) of an antiperspirant salt is calculated as anhydrous weight percent in accordance with the U.S.P. method, as is well known in the art. This calculation excludes any bound water and glycine. In a most preferred embodiment, the antiperspirant product comprises about 10 to about 25 wt. % (USP) aluminum zirconium pentachlorohydrex glycine complex or aluminum zirconium trichlorohydrex glycine complex.

As noted above, the active antiperspirant compound has a surface that has been surface treated with a hydrophobizing agent. Typically, when an antiperspirant user begins to perspire and perspiration is released from sweat glands, particles of the active antiperspirant compound diffuse into the sweat glands and hydrolyze, where they form a plug to plug the sweat gland. However, by surface treating the active antiperspirant compound with the hydrophobizing agent, the particles of the active antiperspirant compound are made more hydrophobic than untreated particles. In this regard, the hydrophobizing agent delays hydrolyzation of the particles, thus permitting the particles to diffuse deeper into the sweat glands before forming plugs, and more effectively preventing perspiration. The hydrophobization agent comprises any material that increases the hydrophobicity of the active antiperspirant compound and that does not adversely affect the phase, thermal or chemical stability of the resulting antiperspirant product. In a preferred embodiment, the hydrophobizing agent comprises isopropyl titanium triisostearate (ITT), methicones, such as, for example hydrogen dimethicone, trimethylsiloxysilicate, or any combination thereof. In one embodiment, the active antiperspirant compound is coated with the hydrophobization agent in an amount of from about 0.2 to about 5 wt. % of the antiperspirant product. Preferably, the active antiperspirant compound is coated with about 1 to about 2 wt. % of the hydrophobizing agent.

Further included in the antiperspirant product is at least one structurant and/or gellant (hereinafter referred collectively as "structurant") that facilitates the solid consistency of the antiperspirant stick product. Naturally-occurring or synthetic waxy materials or combinations thereof can be used as such structurants. Suitable structurants, including waxes and gellants, are often selected from fatty alcohols often containing from 12 to 30 carbons, such as stearyl alcohol, behenyl alcohol and sterols such as lanosterol. As used herein, the term "fatty" means a long chain aliphatic group, such as at least 8 or 12 linear carbons, which is frequently not branched (linear) and is typically saturated, but which can alternatively be branched and/or unsaturated. It is possible for the fatty acid to contain a hydroxyl group, as in 12-hydroxystearic acid, for example as part of a gellant combination, and to employ amido or ester derivates thereof.

Other structurants can comprise hydrocarbon waxes such as paraffin waxes, microcrystalline waxes, ceresin, squalene, and polyethylene waxes. Other suitable structurants are waxes derived or obtained from plants or animals such as hydrogenated castor oil, hydrogenated soybean oil, carnabau, spermacetti, candelilla, beeswax, modified beeswaxes, and Montan wax and individual waxy components thereof. It is especially suitable herein to employ a mixture of wax structurants. Suitable mixtures of structurants can reduce the visibility of active antiperspirant compounds deposited on the skin and result in either a soft solid or a firm solid. In an exemplary embodiment, the surfactant(s) comprise about 10 to about 35 wt. % of the total antiperspirant product. In a preferred embodiment, the antiperspirant product comprises a mixture of stearyl alcohol and hydrogenated castor oil. In a more preferred embodiment, the antiperspirant product comprises about 12 to about 25 wt. % stearyl alcohol and about 1.5 to about 7 wt. % hydrogenated castor oil. In a most preferred embodiment, the antiperspirant product comprises about 15-22 wt. % stearyl alcohol and about 2.8 wt. % hydrogenated castor oil.

The antiperspirant products also may comprise a high refractive index (R.I.) hydrophobic compound. As used herein, the term "high refractive index" means a refractive index of no less than about 1.4. The high R.I. hydrophobic compound also facilitates the minimization and/or prevention of a white residue on the skin by masking the active antiperspirant salt that stays upon the skin upon evaporation of a carrier, described in more detail below. Examples of high R.I. hydrophobic compounds for use in the antiperspirant products include PPG-14 butyl ether, $C_{12}$-$C_{15}$ alkyl benzoate, such as Finsolv TN® available from Innospec of the United Kingdom, and phenyl dimethicone. In a preferred embodiment, the antiperspirant product comprises PPG-14 butyl ether and, in a more preferred embodiment, the antiperspirant product comprises PPG-14 butyl ether in an amount of about 5 to about 15 wt. % of the total antiperspirant product.

In another exemplary embodiment, the antiperspirant product comprises one or more suspending agents that facilitate suspension of the active antiperspirant compound in the antiperspirant product, thereby minimizing the amount of active antiperspirant compound that settles out of the antiperspirant product during manufacture. Suitable suspending agents include clays and silicas. Examples of suitable silicas include fumed silicas and silica derivatives, such as silica dimethyl silylate. Suitable clays include bentonites, hectorites and colloidal magnesium aluminum silicates. In one exemplary embodiment, the antiperspirant product comprises about 0.2 to about 2.5 wt. % suspending agents. In another exemplary embodiment, the antiperspirant product comprises a mixture of silica and silica dimethyl silylate. In a preferred embodiment, the antiperspirant product comprises from about 0.1-0.5 wt. % silica and from about 0.1 to about 2 wt. % silica dimethyl silylate.

In addition to the ingredients identified above, the antiperspirant product may comprise additives, such as those used in conventional antiperspirants. These additives include, but are not limited to, fragrances, including encapsulated fragrances, dyes, pigments, preservatives, antioxidants, moisturizers, and the like. These optional ingredients can be included in the antiperspirant product in an amount of from 0 to about 20 wt. %. In a preferred embodiment, the antiperspirant product comprises myristyl myristate, which provides a conditioning effect to the skin.

The antiperspirant product further comprises at least one hydrophobic carrier. An example of suitable hydrophobic carriers includes liquid siloxanes and particularly volatile polyorganosiloxanes, that is, liquid materials having a measurable vapor pressure at ambient conditions. The polyorganosiloxanes can be linear or cyclic or mixtures thereof. The linear volatile silicones generally have viscosities of less than about 5 centistokes at 25° C., while the cyclic volatile silicones have viscosities under 10 centistokes. Preferred siloxanes include cyclomethicones, which have from about 3 to about 6 silicon atoms, such as cyclotetramethicone, cyclopentamethicone, and cyclohexamethicone, and mixtures thereof. The carrier also may comprise, additionally or alternatively, nonvolatile silicones such as dimethicone and dimethicone copolyols, which have from about 2 to about 9 silicon atoms. Examples of suitable dimethicone and dimethicone copolyols include polyalkyl siloxanes, polyalkylaryl siloxanes, and polyether siloxane copolymers.

Various methods can be used to coat particles of an active antiperspirant compound with a hydrophobizing agent. In one exemplary embodiment, the active antiperspirant compound is combined with a liquid medium sufficient to form a slurry and the hydrophobizing agent. Liquid mediums suitable for forming a slurry with the active antiperspirant compound include, but are not limited to, isopropyl alcohol, heptane, isoheptane, isooctane, isononane, petroleum distillates such as those available from Phillips Chemical under the trade names or trademarks Soltrol 130, Soltrol 150 and Soltrol 170, and combinations thereof. The slurry is thoroughly mixed and then filtered. The filtered, coated active antiperspirant compound is then dried to remove the solvent and any byproduct from the surface. Drying is preferably performed at temperatures in the range of from about 60 to about 90° C., as the active antiperspirant compound may be unstable at temperatures above 90° C. Drying can be achieved passively by exposure to the ambient atmosphere, by using heat for a time effective to yield a dry powder, by vacuum, or the like.

In another exemplary embodiment for surface treating an active antiperspirant compound, a mixture of the hydrophobizing agent and the liquid medium and, optionally, the active antiperspirant compound, is sprayed onto a fluidized or agitated filler bed of active antiperspirant compound. The sprayed active antiperspirant compound is then transferred to a blender and mixing, preferably high shear mixing, is performed for a time sufficient to permit coating of the active antiperspirant compound. The coated active antiperspirant compound is then removed from the blender, filtered if necessary, and dried to remove the solvent and any byproduct from the surface. Again, drying is preferably performed at temperatures in the range of from about 60 to about 90° C., as the active antiperspirant compound may be unstable at temperatures above 90° C. Drying can be achieved passively by exposure to the ambient atmosphere, by using heat for a time effective to yield a dry powder, by vacuum, or the like.

The antiperspirant product, according to various embodiments, can be prepared by combining an active antiperspirant compound coated with a hydrophobizing agent and a carrier at 65-75° C. to form a mixture, pouring the mixture into molds at about 52° C., and cooling the mixture to room temperature. In a preferred embodiment, manufacture of the antiperspirant product includes combining suspending agents in the carrier. Any suitable form of mixing can be used to combine the ingredients, such as high shear mixing, stirring, agitation, blending, or any combination thereof. The surface-treated active antiperspirant compound is added to the suspending agents and carrier to form a premix. Mixing continues until the premix is homogenous and fluid in consistency. In another mixing vessel, the structurants and the high refractive index (R.I.) hydrophobic compound, if used, are added and heat not exceeding 85° C. is applied to melt the ingredients. As the ingredients melt, agitation is slowly commenced. The mixture is cooled to 64-69° C., if necessary, and, with continuous agitation, the premix is incrementally added to the mixture until the mixture is homogenous. Additional carrier is added to the mixture with agitation such that the mixture is maintained at a temperature of 60° C. Additives, such as fragrance, dyes, corn starch, etc. are added with mixing while maintaining the mixture at 60° C. The final mixture is cooled to 52° C., poured into molds, and then allowed to cool to room temperature. As used herein, the term "allowed to cool" means exposing the mixture to room temperature for a time sufficient for the mixture to come to room temperature or exposing the mixture to a refrigerator or cooling room, fan, or other cooling mechanism that lowers the temperature of the mixture to room temperature.

The following are exemplary embodiments of an antiperspirant product contemplated herein, with each of the components set forth in weight percent of the antiperspirant product. The examples are provided for illustration purposes only and are not meant to limit the various embodiments of the antiperspirant product in any way.

Example 1

| Ingredient | Wt. % |
|---|---|
| Cyclopentasiloxane | 40.95 |
| AAZG-531-ITT1 | 22.76 |
| Stearyl Alcohol | 20.00 |
| PPG-14 butyl ether | 9.80 |
| Hydrogenated castor oil | 2.84 |
| Myristyl Myristate | 1.92 |
| Silica dimethyl silylate | 1.38 |
| Silica | 0.35 |
| Total | 100.00, | where AAZG-531-ITT1 is aluminum zirconium trichlorohydrex glycine complex (AAZG-531) surface treated with 1 wt % ITT. AAZG-531 is available from Summit Reheis of Huguenot, N.Y.

Example 2

| Ingredient | Wt. % |
|---|---|
| Cyclopentasiloxane | 40.72 |
| AAZG-531-TMS2 | 22.99 |
| Stearyl Alcohol | 20.00 |
| PPG-14 butyl ether | 9.80 |

-continued

| Ingredient | Wt. % |
| --- | --- |
| Hydrogenated castor oil | 2.84 |
| Myristyl Myristate | 1.92 |
| Silica dimethyl silylate | 1.38 |
| Silica | 0.35 |
| Total | 100.00, | where AAZG-531-TMS2 is the active antiperspirant compound (AAZG-531) surface treated with 2 wt % trimethylsiloxysilicate.

Example 3

| Ingredient | Wt. % |
| --- | --- |
| Cyclopentasiloxane | 40.72 |
| AAZG-531-DMC2 | 22.99 |
| Stearyl Alcohol | 20.00 |
| PPG-14 butyl ether | 9.80 |
| Hydrogenated castor oil | 2.84 |
| Myristyl Myristate | 1.92 |
| Silica dimethyl silylate | 1.38 |
| Silica | 0.35 |
| Total | 100.00, | where AAZG-531-DMC2 is the active antiperspirant compound (AAZG-531) surface treated with 2 wt % hydrogen dimethicone.

Examples 1, 2, and 3 were prepared by coating AAZG-531 with ITT, trimethylsiloxysilicate, and hydrogen dimethicone, respectively. About 90% of the cyclopentasiloxane was added to a mixing container and agitation was initiated. With continuous agitation, the silica and the silica dimethyl silylate were added incrementally to the cyclopentasiloxane until the silicas were wetted. Next, utilizing high shear mixing, a premix was formed by incrementally adding the surface-treated active antiperspirant compound until the premix had a consistently fluid appearance void of any particulates.

In another mixing container, the hydrogenated castor oil, stearyl alcohol, PPG-14 butyl ether, and myristyl myristate were added and heat was slowly initiated to melt the components while agitation was performed as the mix became molten. The temperature of the mixture did not exceed 85° C. With continuous agitation, the premix was incrementally added while the mixture was maintained at a batch temperature of from about 64 to about 69° C. Agitation was continued until the mixture was homogeneous. The remainder of the cyclopentasiloxane was added to the mixture with agitation, while the mixture was maintained at a temperature of about 60° C. The mixture was cooled to about 52° C., and then was poured into molds and allowed to cool to room temperature.

Accordingly, antiperspirant products with active antiperspirant compounds surface treated with hydrophobizing agents have been provided. In various embodiments, the antiperspirant products exhibit enhanced antiperspirant efficacy. In addition, or alternatively, the antiperspirant products exhibit improved "skin feel." That is, when applied to the skin of a user, the antiperspirant product exhibits reduced slipperiness, i.e., reduced slip between the underarms, and improved glide. The antiperspirant products also exhibit improved evenness of coverage. While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An antiperspirant product comprising:
an active antiperspirant compound with a coating of a hydrophobizing agent comprising isopropyl titanium triisostearate; and
a hydrophobic carrier.

2. The antiperspirant product of claim 1, wherein the hydrophobizing agent further comprises a material selected from the group consisting of methicones, trimethylsiloxysilicate, and any combination thereof.

3. The antiperspirant product of claim 1, wherein the active antiperspirant compound is coated with the hydrophobizing agent in an amount of from about 0.2 to about 5 wt. % of the antiperspirant product.

4. The antiperspirant product of claim 3, wherein the active antiperspirant compound is coated with the hydrophobizing agent in an amount of from about 1 to about 2 wt. % of the antiperspirant product.

5. The antiperspirant product of claim 1, wherein the hydrophobic carrier comprises siloxanes.

6. The antiperspirant product of claim 5, wherein the hydrophobic carrier comprises a cyclomethicone.

7. The antiperspirant product of claim 1, further comprising a structurant.

8. The antiperspirant product of claim 7, wherein the structurant is stearyl alcohol.

9. The antiperspirant product of claim 1, wherein the active antiperspirant compound comprises a material selected from the group consisting of aluminum zirconium trichlorohydrex glycine complex, aluminum zirconium pentachlorohydrex glycine complex, aluminum zirconium tetrachlorohydrate glycine complex, and aluminum zirconium octachlorohydrex glycine complex.

10. The antiperspirant product of claim 1, wherein the active antiperspirant compound is present in an amount of from about 10 to about 25 wt. % of the antiperspirant product.

11. An antiperspirant product comprising:
an active antiperspirant compound surface treated with a hydrophobizing agent comprising isopropyl titanium triisostearate;
a hydrophobic carrier;
stearyl alcohol;
hydrogenated castor oil; and
a suspending agent.

12. The antiperspirant product of claim 11, wherein the hydrophobizing agent further comprises a material selected from the group consisting of methicones, trimethylsiloxysilicate, and any combination thereof.

13. The antiperspirant product of claim 11, wherein the active antiperspirant compound is coated with the hydrophobizing agent in an amount of from about 0.2 to about 5 wt. % of the antiperspirant product.

14. The antiperspirant product of claim 13, wherein the active antiperspirant compound is coated with the hydrophobizing agent in an amount of from about 1 to about 2 wt. % of the antiperspirant product.

* * * * *